US010292849B2

(12) United States Patent
Boyle et al.

(10) Patent No.: US 10,292,849 B2
(45) Date of Patent: *May 21, 2019

(54) BALLOON CATHETER HAVING METAL BALLOON AND METHOD OF MAKING SAME

(71) Applicant: VACTRONIX SCIENTIFIC, INC., Fremont, CA (US)

(72) Inventors: Christopher T. Boyle, Flushing, NY (US); Steven R. Bailey, San Antonio, TX (US); Christopher E. Banas, Breckenridge, CO (US); Julio C. Palmaz, Napa, CA (US)

(73) Assignee: Vactronix Scientific, LLC, Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/290,833

(22) Filed: Oct. 11, 2016

(65) Prior Publication Data
US 2017/0095362 A1    Apr. 6, 2017

Related U.S. Application Data

(60) Continuation of application No. 13/587,821, filed on Aug. 16, 2012, now Pat. No. 9,463,305, which is a
(Continued)

(51) Int. Cl.
*A61F 2/958* (2013.01)
*A61M 25/10* (2013.01)
(Continued)

(52) U.S. Cl.
CPC .............. *A61F 2/958* (2013.01); *A61F 2/82* (2013.01); *A61F 2/91* (2013.01); *A61M 25/104* (2013.01);
(Continued)

(58) Field of Classification Search
CPC .... A61M 2025/1013; A61M 2025/105; A61M 2025/1075; A61M 2025/1088; A61M 2025/1029
(Continued)

(56) References Cited

U.S. PATENT DOCUMENTS 4,885,003 A  *  12/1989  Hillstead ........ A61B 17/320725
                                                        604/22
5,002,560 A       3/1991  Machold et al. ............. 606/198
(Continued)

FOREIGN PATENT DOCUMENTS

JP       06-188135    5/1986    ............. G01N 27/30
JP       02-502613    8/1990    ............. A61M 25/00
(Continued)

OTHER PUBLICATIONS

Busch, J.D., et al., "Shape Memory Properties in NiTI Sputter-deposited Film", *J Appl. Phys* 68(12): 6224-6226 (1990).
(Continued)

*Primary Examiner* — Martin T Ton
(74) *Attorney, Agent, or Firm* — David G. Rosenbaum; Benjamin D. Rotman; Rosenbaum IP, P.C.

(57) ABSTRACT

A metal balloon catheter having a main tubular body, a metal balloon proximate a distal end of the main tubular body, a central annulus extending along an entire longitudinal aspect of the catheter for accommodating a guidewire therethrough and an inflation annulus adjacent the central annulus which extends along the longitudinal axis of the main tubular body and terminates in fluid flow communication with an inflation chamber of the metal balloon. The metal balloon catheter may be either unitary integral metal catheter in which the main tubular body and the balloon are fabricated of metal, or it may consist of a polymeric main tubular body and a metal balloon.

8 Claims, 4 Drawing Sheets

Related U.S. Application Data division of application No. 10/693,572, filed on Oct. 24, 2003, now Pat. No. 8,460,333, which is a continuation of application No. 10/135,582, filed on Apr. 29, 2002, now Pat. No. 6,733,513, and a continuation-in-part of application No. 09/443,929, filed on Nov. 19, 1999, now Pat. No. 6,379,383.

(60) Provisional application No. 60/309,406, filed on Jul. 31, 2001.

(51) Int. Cl.
- *A61F 2/82* (2013.01)
- *A61F 2/91* (2013.01)
- *A61B 17/00* (2006.01)
- *A61B 17/22* (2006.01)

(52) U.S. Cl.
CPC .... *A61M 25/1029* (2013.01); *A61M 25/1038* (2013.01); *A61B 2017/00862* (2013.01); *A61B 2017/22054* (2013.01); *A61F 2002/9583* (2013.01); *A61F 2210/0076* (2013.01); *A61F 2230/005* (2013.01); *A61F 2230/006* (2013.01); *A61F 2310/00395* (2013.01); *A61M 25/1034* (2013.01); *A61M 2025/105* (2013.01); *A61M 2025/1013* (2013.01); *A61M 2025/1031* (2013.01); *A61M 2025/1075* (2013.01); *A61M 2025/1086* (2013.01); *A61M 2025/1088* (2013.01); *A61M 2025/1097* (2013.01); *Y10S 977/845* (2013.01)

(58) Field of Classification Search
USPC ...... 604/101.01, 12, 107; 606/191, 192, 194
See application file for complete search history.

(56) References Cited

U.S. PATENT DOCUMENTS

| | | | | |
|---|---|---|---|---|
| 5,061,267 | A | 10/1991 | Zeiher | 606/40 |
| 5,456,667 | A | 10/1995 | Ham et al. | 604/107 |
| 5,478,320 | A | 12/1995 | Trotta | 604/96 |
| 5,505,700 | A | 4/1996 | Leone et al. | 604/96 |
| 5,514,092 | A * | 5/1996 | Forman | A61M 25/1011 604/101.03 |
| 5,605,714 | A | 2/1997 | Dearnaley et al. | 427/2.24 |
| 5,607,445 | A | 3/1997 | Summers | 606/198 |
| 5,607,463 | A | 3/1997 | Schwartz et al. | 623/1 |
| 5,609,629 | A | 3/1997 | Fearnot et al. | 623/1 |
| 5,628,788 | A | 5/1997 | Pinchuk | 623/1 |
| 5,630,840 | A | 5/1997 | Mayer | 623/1 |
| 5,647,858 | A | 7/1997 | Davidson | 604/264 |
| 5,649,951 | A | 7/1997 | Davidson | 606/198 |
| 5,649,977 | A | 7/1997 | Campbell | 623/1 |
| 5,656,036 | A | 8/1997 | Palmaz | 623/12 |
| 5,658,515 | A | 8/1997 | Lee et al. | 264/219 |
| 5,683,453 | A | 11/1997 | Palmaz | 623/1 |
| 5,685,961 | A | 11/1997 | Pourrezaei et al. | 204/192.15 |
| 5,690,670 | A | 11/1997 | Davidson | 606/198 |
| 5,704,908 | A | 1/1998 | Hofmann et al. | 604/21 |
| 5,723,219 | A | 3/1998 | Kolluri et al. | 428/411.1 |
| 5,725,573 | A | 3/1998 | Dearnaley et al. | 623/2 |
| 5,728,150 | A | 3/1998 | McDonald et al. | 623/1 |
| 5,728,158 | A | 3/1998 | Lau et al. | 623/12 |
| 5,733,303 | A | 3/1998 | Israel et al. | 606/198 |
| 5,735,896 | A | 4/1998 | Amon et al. | 623/11 |
| 5,744,515 | A | 4/1998 | Clapper | 523/113 |
| 5,765,418 | A | 6/1998 | Rosenberg | 72/47 |
| 5,772,864 | A | 6/1998 | Møller et al. | 205/73 |
| 5,776,161 | A | 7/1998 | Globerman | 606/194 |
| 5,782,908 | A | 7/1998 | Cahalan et al. | 623/1 |
| 5,782,910 | A | 7/1998 | Davidson | 623/3 |
| 5,788,558 | A | 8/1998 | Klein | 451/36 |
| 5,792,172 | A | 8/1998 | Fischell et al. | 606/198 |
| 5,811,151 | A | 9/1998 | Hendriks et al. | 427/2.24 |
| 5,824,045 | A | 10/1998 | Alt | 623/1 |
| 5,824,049 | A | 10/1998 | Ragheb et al. | 623/1 |
| 5,824,054 | A | 10/1998 | Khosravi et al. | 623/1 |
| 5,824,056 | A | 10/1998 | Rosenberg | 623/1 |
| 5,840,009 | A | 11/1998 | Fischell et al. | 600/3 |
| 5,843,117 | A | 12/1998 | Alt et al. | 606/194 |
| 5,843,120 | A | 12/1998 | Israel et al. | 606/198 |
| 5,843,289 | A | 12/1998 | Lee et al. | 204/192.3 |
| 5,849,206 | A | 12/1998 | Amon et al. | 216/63 |
| 5,855,600 | A | 1/1999 | Alt | 623/1 |
| 5,855,802 | A | 1/1999 | Acciai et al. | 216/8 |
| 5,855,955 | A | 1/1999 | Claar et al. | 427/248.1 |
| 5,858,556 | A | 1/1999 | Eckert et al. | 428/586 |
| 5,866,113 | A | 2/1999 | Hendriks et al. | 424/78.17 |
| 5,868,782 | A | 2/1999 | Frantzen | 606/198 |
| 5,873,904 | A | 2/1999 | Ragheb et al. | 623/1 |
| 5,876,432 | A | 3/1999 | Lau et al. | 623/1 |
| 5,879,370 | A | 3/1999 | Fischell et al. | 606/198 |
| 5,891,507 | A | 4/1999 | Jayaraman | 427/2.25 |
| 5,895,406 | A | 4/1999 | Gray et al. | 606/198 |
| 5,899,935 | A | 5/1999 | Ding | 623/1 |
| 5,907,893 | A | 6/1999 | Zadno-Azizi et al. | 29/6.1 |
| 5,913,896 | A | 6/1999 | Boyle et al. | 623/1 |
| 5,919,225 | A | 7/1999 | Lau et al. | 623/1 |
| 5,925,063 | A | 7/1999 | Khosravi | 606/200 |
| 5,932,299 | A | 8/1999 | Katoot | 427/508 |
| 5,938,682 | A | 8/1999 | Hojeibane et al. | 606/198 |
| 5,938,697 | A | 8/1999 | Killion et al. | 623/1 |
| 5,945,153 | A | 8/1999 | Dearnaley | 427/2.12 |
| 5,951,881 | A | 9/1999 | Rogers et al. | 216/41 |
| 5,955,588 | A | 9/1999 | Tsang et al. | 536/21 |
| 5,962,138 | A | 10/1999 | Kolluri et al. | 428/411.1 |
| 5,968,091 | A | 10/1999 | Pinchuk et al. | 623/1 |
| 5,972,018 | A | 10/1999 | Israel et al. | 606/198 |
| 5,972,027 | A | 10/1999 | Johnson | 623/1 |
| 5,972,441 | A | 10/1999 | Campbell et al. | 428/34.1 |
| 5,984,905 | A | 11/1999 | Dearnaley | 604/265 |
| 5,993,374 | A | 11/1999 | Kick | 600/8 |
| 6,007,573 | A | 12/1999 | Wallace et al. | 623/1 |
| 6,013,054 | A | 1/2000 | Jiun Yan | 604/96 |
| 6,013,855 | A | 1/2000 | McPherson et al. | 623/11 |
| 6,015,429 | A | 1/2000 | Lau et al. | 623/1 |
| 6,019,784 | A | 2/2000 | Hines | 623/1 |
| 6,022,370 | A | 2/2000 | Tower | 606/194 |
| 6,027,526 | A | 2/2000 | Limon et al. | 623/1 |
| 6,033,433 | A | 3/2000 | Ehr et al. | 623/1 |
| 6,042,597 | A | 3/2000 | Kveen et al. | 606/198 |
| 6,042,605 | A | 3/2000 | Martin et al. | 623/1 |
| 6,056,776 | A | 5/2000 | Lau et al. | 623/1.16 |
| 6,059,808 | A | 5/2000 | Boussignac et al. | 606/191 |
| 6,066,167 | A | 5/2000 | Lau et al. | 623/1 |
| 6,066,168 | A | 5/2000 | Lau et al. | 623/1.16 |
| 6,066,169 | A | 5/2000 | McGuinness | 623/1.16 |
| 6,071,305 | A | 6/2000 | Brown et al. | 623/1 |
| 6,086,773 | A | 7/2000 | Dufresne et al. | 216/8 |
| 6,096,175 | A | 8/2000 | Roth | 204/192.15 |
| 6,103,320 | A | 8/2000 | Matsumoto et al. | 427/535 |
| 6,106,642 | A | 8/2000 | DiCarlo et al. | 148/563 |
| 6,113,750 | A | 9/2000 | Shinmura et al. | 204/192.12 |
| 6,120,536 | A | 9/2000 | Ding et al. | 623/1.43 |
| 6,120,847 | A | 9/2000 | Yang et al. | 427/335 |
| 6,124,523 | A | 9/2000 | Banas et al. | 623/11 |
| 6,136,258 | A | 10/2000 | Wang et al. | 264/514 |
| 6,164,283 | A * | 12/2000 | Lesh | A61B 18/10 128/898 |
| 6,190,404 | B1 | 2/2001 | Palmaz et al. | 623/1.15 |
| 6,202,304 | B1 | 3/2001 | Shatz | 29/896.6 |
| 6,207,536 | B1 | 3/2001 | Matsumoto et al. | 438/478 |
| 6,231,572 | B1 | 5/2001 | Hart et al. | 606/45 |
| 6,245,104 | B1 | 6/2001 | Alt | 623/1.46 |
| 6,264,687 | B1 | 7/2001 | Tomonto | 623/1.16 |
| 6,274,016 | B1 | 8/2001 | Matsumoto et al. | 204/298.11 |
| 6,280,467 | B1 | 8/2001 | Leonhardt | 623/1.16 |
| 6,287,277 | B1 | 9/2001 | Yan | 604/96.01 |
| 6,287,329 | B1 | 9/2001 | Duerig et al. | 623/1.11 |
| 6,287,435 | B1 | 9/2001 | Drewery et al. | 204/298.09 |
| 6,287,628 | B1 | 9/2001 | Hossainy et al. | 427/2.3 |
| 6,290,720 | B1 | 9/2001 | Khosravi et al. | 623/1.13 |

(56) References Cited

U.S. PATENT DOCUMENTS

| | | | |
|---|---|---|---|
| 6,290,721 B1 | 9/2001 | Heath | 623/1.15 |
| 6,293,967 B1 | 9/2001 | Shanley | 623/1.15 |
| 6,299,604 B1 | 10/2001 | Ragheb et al. | 604/265 |
| 6,312,463 B1 | 11/2001 | Rourke et al. | 623/1.39 |
| 6,315,708 B1 | 11/2001 | Salmon et al. | 600/3 |
| 6,315,794 B1 | 11/2001 | Richter | 623/1.34 |
| 6,331,191 B1 | 12/2001 | Chobotov | 623/1.44 |
| 6,458,142 B1 | 10/2002 | Khosravi et al. | 623/1.13 |
| 6,942,680 B2 * | 9/2005 | Grayzel | A61F 2/958 606/159 |
| 2001/0000188 A1 | 4/2001 | Lenker et al. | 623/1.13 |
| 2001/0019847 A1 | 9/2001 | Mori et al. | 438/2 |
| 2001/0021870 A1 | 9/2001 | Edwin et al. | 623/1.13 |
| 2001/0025131 A1 | 9/2001 | Edwin et al. | 600/36 |
| 2001/0032013 A1 | 10/2001 | Marton | 623/1.15 |
| 2001/0037144 A1 | 11/2001 | Kim et al. | 623/1.15 |
| 2001/0039449 A1 | 11/2001 | Johnson et al. | 623/1.19 |
| 2002/0013616 A1 | 1/2002 | Carter et al. | 623/1.15 |

FOREIGN PATENT DOCUMENTS

| | | | |
|---|---|---|---|
| JP | 07-047135 | 2/1995 | A61M 29/02 |
| JP | 2000-508220 | 4/2000 | A61N 1/30 |
| JP | 2001-504359 | 4/2001 | A61F 2/958 |
| WO | WO 1989/005609 | 6/1989 | A61B 17/22 |
| WO | WO 1997/044692 | 11/1997 | G02B 6/16 |
| WO | WO 1998/013537 | 4/1998 | C25D 1/00 |
| WO | WO 1998/045506 | 10/1998 | C25D 7/04 |
| WO | WO 1999/016385 | 4/1999 | A61F 2/06 |
| WO | WO 1999/023977 | 5/1999 | A61F 2/06 |
| WO | WO 2000/004204 | 1/2000 | C23C 14/34 |
| WO | WO 2000/018327 | 4/2000 | A61F 2/06 |
| WO | WO 2000/054704 | 9/2000 | A61F 2/06 |
| WO | WO 2001/021851 | 3/2001 | C23C 14/34 |
| WO | WO 2001/021852 | 3/2001 | C23C 14/34 |
| WO | WO 2001/037892 | 5/2001 | A61L 2/06 |
| WO | WO 2001/043790 | 6/2001 | A61L 33/02 |
| WO | WO 2001/049340 | 7/2001 | A61L 31/18 |
| WO | WO 2001/053559 | 7/2001 | C23C 14/14 |
| WO | WO 2001/055473 | 8/2001 | C23C 14/00 |
| WO | WO 2001/056502 | 8/2001 | A61F 2/06 |

OTHER PUBLICATIONS

Buchaillot, L., et al., "Constitutive Parts of a Shape Memory Alloy Titanium Nickel Thin Film Catheter" *Proceedings of the Second International Conference on Shape Memory and Superelastic Technologies Asilomar Conference Center*, Pacific Grove, California, USA, pp. 183-188 (1997).
Curtis, et al., "Reactions of Biological Cells to Nanostructures" *AVS 46th International Symposium*, Paper BI-WeM2 (1999).
Daw, R., et al., "Endothelial Cell Organization on Micropatterned Protein Surfaces", *AVS 47th International Symposium*, Paper No. BI-WeP21 (2000).
Ensinger, W., "The influence of ion irradiation during film growth on the chemical stability of film/substrate systems" *Surface and Coatings Technology*, 80: 35-48 (1996).
Fancey, K.S., et al., "Relative importance of bombardment energy and intensity in ion plating" (Abstract) *Journal of Vacuum Science & Technology A: Vacuum, Surfaces and Films*, 13(2): 428-435 (1995).
Goldberg, F., et al., "The effects of ion irradiation on NiTi shape memory alloy thin films" *Proceedings of the Second International Conference on Shape Memory and Superelastic Technologies Asilomar Conference Center*, Pacific Grove, California, USA, pp. 177-182 (1997).
Houston, J.E., "The nanomechanical properties of thin films" *AVS 47th International Symposium*, Paper No. TF-TuA1 (2000).
Ishida, A., et al., "Microstructure of T-rich TiNi thin films" *Proceedings of the Second International Conference on Shape Memory Superelastic Technologies Asilomar Conference*, Pacific Grove, California, USA, pp. 161-166 (1997).
Johnson, A.D., et al., "Recent progress in the application of thin film shape memory alloys" *Proceedings of the First International Conference on Shape Memory and Superelastic Technologies Asilomar Conference Center*, Pacific Grove, California, USA, pp. 299-310 (1994).
Johnson, A.D., et al., "Applications of shape-memory alloy thin films" *Proceedings of the Second International Conference on Shape Memory and Superelastic Technologies Asilomar Conference Center*, Pacific Grove, California, USA, pp. 1-8 (1997).
Kusano, E., et al., "Anomalous plastic and elastic behaviors of sputter-deposited TiN with 10 or 20 inserted thin Al layers evaluated by nanoindentation", *AVS 47th International Symposium*, Paper No. TF-TuA3 (2000).
Mrksich, M., "Model surfaces for studying and controlling the adhesion of cells" *AVS 47th International Symposium*, Invited Paper No. BI+ EL-TuA1 (2000).
Nishikawa, T., et al., "Tissue formation of hepatocytes on microporous films of polylactide", *AVS 47th International Symposium*, Paper No. BI+EL-TuA10 (2000).
Pingshan, Q., et al., "The effect of HCD technological factors on the NiTi SMA film thickness" *Proceedings of the Second International Conference on Shape Memory and Superelastic Technologies Asilomar Conference Center*, Pacific Grove, California, USA, pp. 173-176 (1997).
Quandt, E., et al., "Sputter-deposition of TiNi, TiNiPd and TiPd films displaying the two-way shape-memory effect" *Sensors and Actuators*, A 53, pp. 434-436 (1996).
Sutherland, D.S., et al., "Cell response to chemically and topographically modified surfaces" *AVS 47th International Symposium*, Paper No. BI+EL-TuA3 (2000).
AVS 46th International Symposium, Paper BI-WeM5, "Biocompatibility of cardiac cells on silane-modified surfaces" (1999).
AVS 46th International Symposium, Paper No. BI-FrM10, "Biofilm—titanium chemistry of adhesion using x-ray photoelectron spectroscopy" (1999).
AVS 46th International Symposium, Paper No. BI-WeM7, "Biofunctionalization of surfaces with peptide amphilphiles" (1999).
AVS 46th International Symposium, Paper No. BI-FrM10, "Nanoscale patterning of gold for attachment of supported lipid bilayers" (1999).
AVS 46th International Symposium, Paper No. Paper BI-WeM9, "Plasma copolymer surfaces for cell culture" (1999).
AVS 46th International Symposium, Paper No. BI-FrM2, "Plasma co-polymer surfaces for the controlled adsorption of common proteins" (1999).
IBM Technical Disclosure Bulletin, "Multicomponent film deposition by target biasing", pp. 1-2 (1980).
Ion Beam-Assisted, Electron Beam Physical Vapor (EB-PVD) Deposition, Penn State Applied Research Laboratory, "Multilayer ceramic/metallic coatings" pp. 1-4 (1997).

* cited by examiner

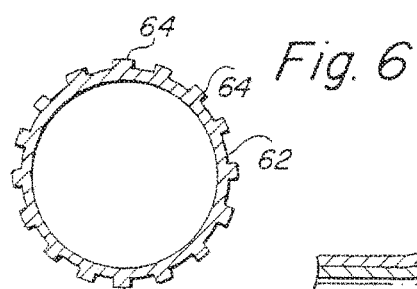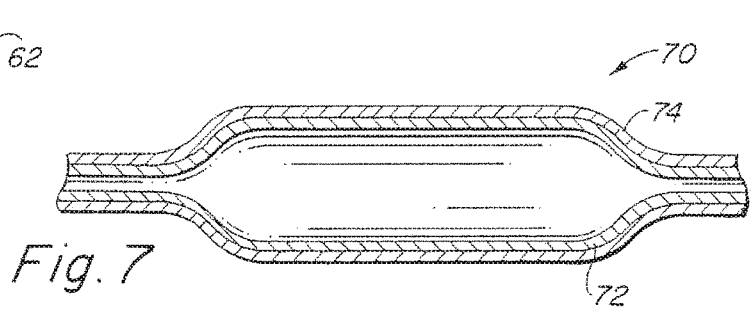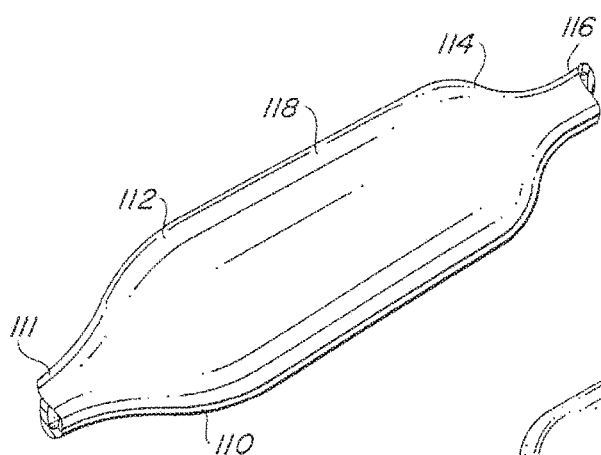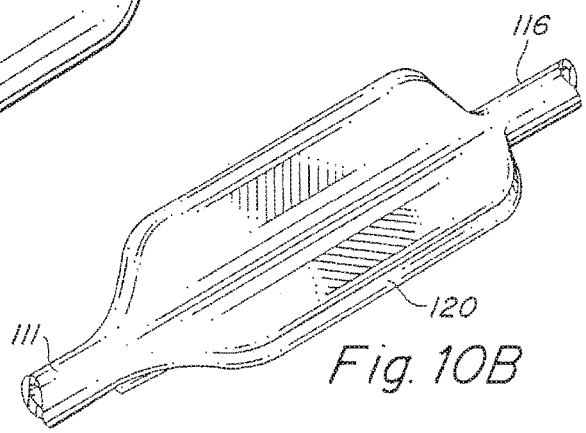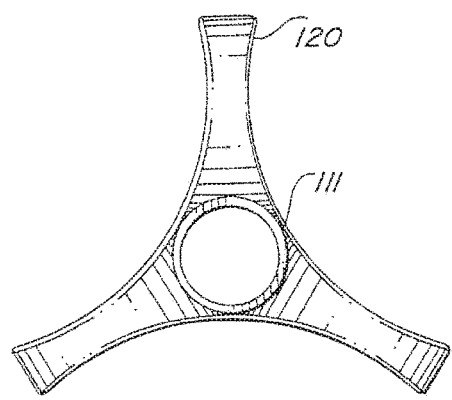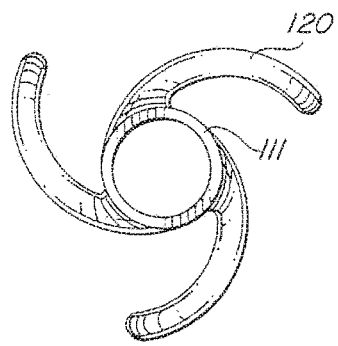

BALLOON CATHETER HAVING METAL BALLOON AND METHOD OF MAKING SAME

CROSS-REFERENCE TO RELATED APPLICATIONS

The present application is a continuation of commonly assigned U.S. patent application Ser. No. 13/587,821, filed Aug. 16, 2012, which issued as U.S. Pat. No. 9,463,305 on Oct. 11, 2016; which is a divisional of commonly assigned U.S. patent application Ser. No. 10/693,572, filed Oct. 24, 2003, which issued as U.S. Pat. No. 8,460,333 on Jun. 11, 2013, which is a continuation of commonly assigned U.S. patent application Ser. No. 10/135,582, filed Apr. 29, 2002, which issued as U.S. Pat. No. 6,733,513 on May 11, 2004, which relates to and claims priority from U.S. Provisional Patent Application Ser. No. 60/309,406 filed Jul. 31, 2001, and is a continuation-in-part of U.S. patent application Ser. No. 09/443,929 filed Nov. 19, 1999, which issued as U.S. Pat. No. 6,379,383 on Apr. 30, 2002.

BACKGROUND OF THE INVENTION

The present invention relates generally to balloon catheters and more specifically to balloon catheters suitable for use in stent delivery, perfusion, drug delivery, angioplasty, valvuloplasty and endartherectomy procedures. More particularly, the present invention pertains to a balloon catheter having a balloon fabricated solely of metal and to a method of making metal balloons.

SUMMARY OF THE INVENTION

It is an object of the present invention to provide a balloon catheter having a metal balloon. It is a further objective of the present invention to provide a method of making a balloon catheter having a metal balloon. The inventive metal balloon catheter consists generally of a catheter comprising a main tubular body, a metal balloon proximate a distal end of the main tubular body, a central annulus extending along an entire longitudinal aspect of the catheter for accommodating a guidewire therethrough and an inflation annulus adjacent the central annulus which extends along the longitudinal axis of the main tubular body and terminates in fluid flow communication with an inflation chamber of the metal balloon. The metal balloon catheter may consist of a unitary integral metal catheter in which the main tubular body and the balloon are fabricated of metal, or it may consist of a polymeric main tubular body and a metal balloon. As with conventional balloon catheters, the inventive metal balloon catheter has standard connectors for coupling conventional balloon catheter accessories.

The inventive metal balloon may assume a wide variety of geometries, including without limitation, tubular coils such as for use in endartherectomy procedures or as perfusion balloons, bifurcated balloons for angioplasty of vascular bifurcations or for delivery of bifurcated implantable devices, and angled balloons that have an angular offset from the longitudinal axis of the catheter. Additionally, because the inventive metal balloon is fabricated of metal, it may be made more or less radiopaque by fabricating the balloon of a radiopaque metal, such as tantalum, or providing regions on the balloon that have a radiopaque metal differentially incorporated thereupon. Moreover, the inventive metal balloon may be used either as a conductor of directly applied electrical energy or inductively energized by external application of energy, such as by ultrasound or magnetic resonance. This conductive property of the inventive metal balloon is particularly useful in diathermy, to return a signal for imaging without an added contrast medium, or return a signal to provide data concerning the in vivo environment.

The inventive metal balloon is preferably fabricated of a biocompatible metal and is formed as a film of material. The inventive metal balloon is not restricted to single layer films, but a plurality of films may be laminated to one another in order to enhance the material, geometric and/or functional properties of the resultant metal balloon. Suitable materials to fabricate the inventive metal balloon are chosen for their biocompatibility, mechanical properties, i.e., tensile strength, yield strength, and their ease of deposition, include, without limitation, the following: titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel.

The inventive metal balloon is preferably fabricated by vacuum deposition techniques. In accordance with the present invention, the preferred deposition methodologies include ion-beam assisted evaporative deposition and sputtering techniques. In ion beam-assisted evaporative deposition it is preferable to employ dual and simultaneous thermal electron beam evaporation with simultaneous ion bombardment of the substrate using an inert gas, such as argon, xenon, nitrogen or neon. Bombardment with an inert gas, such as argon ions serves to reduce void content by increasing the atomic packing density in the deposited material during deposition. The reduced void content in the deposited material is one of the important factors that allow the mechanical properties of that deposited material to be similar to the bulk material properties. Deposition rates up to 20 nm/sec are achievable using ion beam-assisted evaporative deposition techniques.

With the sputtering technique, it is preferable to employ a cylindrical sputtering target, a single circumferential source which concentrically surrounds the substrate which is held in a coaxial position within the source. Other source geometries, including spherical, are also contemplated to best coat substrates with complex geometries including the inventive balloon. Alternate deposition processes which may be employed to form the metal balloon in accordance with the present invention are cathodic arc, laser ablation, and direct ion beam deposition. When employing vacuum deposition methodologies, the crystalline structure of the deposited film affects the mechanical properties of the deposited film. These mechanical properties of the entire deposited film or differential section of the deposited film may be modified by post-process treatment, such as by, for example, annealing, high pressure treatment or gas quenching.

During deposition, the chamber pressure, the deposition pressure and the partial pressure of the process gases are controlled to optimize deposition of the desired species onto the substrate. As is known in the microelectronic fabrication, nano-fabrication and vacuum coating arts, both the reactive and non-reactive gases are controlled and the inert or non-reactive gaseous species introduced into the deposition chamber are typically argon and nitrogen. The substrate may be either stationary or moveable, either rotated about its longitudinal axis, or moved in an X-Y plane within the reactor to facilitate deposition or patterning of the deposited material onto the substrate. The deposited material maybe deposited either as a uniform solid film onto the substrate, or patterned by (a) imparting either a positive or negative pattern onto the substrate, such as by etching or photolithography techniques applied to the substrate surface to create a positive or negative image of the desired pattern or (b) using a mask or set of masks which are either stationary or moveable relative to the substrate to define the pattern applied to the substrate. Patterning may be employed to achieve regions of the metal balloon that exhibit different functional properties, such as providing folding regions that permit low profile folding of the metal balloon for endoluminal delivery, or different geometric properties of the metal balloon, such as recesses in the surface of the metal balloon having mating geometries for nesting a stent. Complex finished geometries and material properties of the resultant metal balloon, both in the context of spatial orientation of the pattern, material thicknesses at different regions of the deposited film, or differences in the crystalline structure of the metal film at different regions of the metal film may be accomplished by employing vacuum deposition techniques and post-process heat treatment of the metal film.

These and other objectives, features and advantages of the present invention will become more apparent to those of ordinary skill in the art from the following more detailed description of the present invention taken with reference to the accompanying figures.

BRIEF DESCRIPTION OF THE FIGURES

FIG. 6 is a cross-sectional view taken along line 6-6 of FIG. 5.

FIG. 7 is a cross-sectional view of a metal balloon embodiment having an elastomeric coating applied thereto.

FIG. 10A is a perspective view of the inventive metal balloon in its inflated state.

FIG. 10B is a perspective view of the inventive metal balloon in its deflated state in accordance with one embodiment of the invention.

FIG. 10C is an end view of the inventive metal balloon in its deflated state.

FIG. 10D is an end view of the inventive metal balloon in its deflated state being folded in accordance with one embodiment of the invention.

DETAILED DESCRIPTION OF THE PREFERRED EMBODIMENTS

Figure 1:
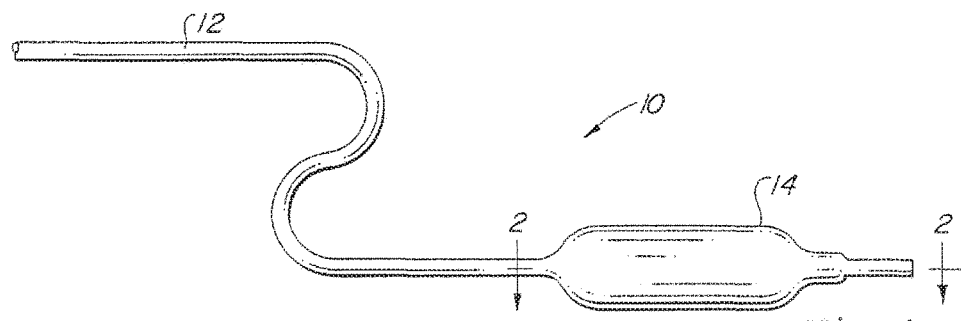
FIG. 1 is a perspective view of the inventive metal balloon catheter.
Figure 2:
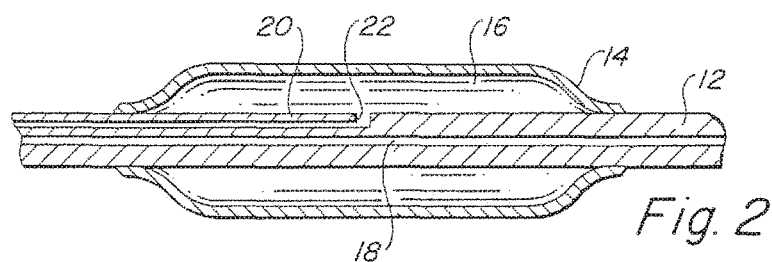
FIG. 2 is a cross-sectional view taken along line 2-2 of FIG. 1.

With particular reference to FIGS. 1-2, the inventive metal balloon catheter 10 consists generally of a primary tubular catheter body member 12 and a balloon 14 situated at a distal end of the metal balloon catheter 10. A proximal end of the metal balloon catheter 10 (not shown) is provided with conventional fittings to couple with conventional balloon catheter control accessories. The body member 12 and the balloon 14 may both be fabricated of biocompatible metal and/or metals, which may be selected from the group consisting of titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nitinol, and stainless steel. Alternatively, the body member 12 may be fabricated of a biocompatible polymer and only the balloon 14 is fabricated of a biocompatible metal, and affixed to the body member 12 using a suitable biocompatible adhesive.

With each of the embodiments of the present invention described herein, the metal balloon 14 may consist of a single layer of a single metal, multiple layers of a single metal or a multiple layers of multiple metals. With a laminated structure, the metal balloon 14 may include one or more radiopaque metals to enhance visualization of the metal balloon 14 under x-ray.

The balloon 14 is coaxially positioned about the body member 12 and defines an inflation lumen 16 between an inner wall of the balloon 14 and the body member 12. As with conventional balloon catheters, the body member 12 is a tubular member and includes an inflation lumen 20 that communicates between the proximal end of the body member 12 and at least one inflation port 22 in fluid flow communication with the inflation lumen of the balloon 14. The inflation lumen 20 may also function as a guidewire lumen, or a discrete guidewire lumen 18 may be provided in the body member 12.

Conventional balloon catheters typically require a large number of inflation ports 22 in order to meet governmental regulatory requirements for inflation and deflation times. However, it has been found with the present invention, that by fabricating the balloon 14 of a biocompatible metal having a wall thickness between 0.1 μ and 25 μ and inflated outer diameters between 0.1 mm and 40 mm, that the regulatory requirements for inflation and deflation times may be met with a single inflation port 22.

By fabricating the balloon 14 of a biocompatible metal, wall thicknesses between 3 μ and 12 μ may be achieved, with the resulting metal balloon 14 exhibiting zero compliance with extremely high tensile strength. An additional advantage resulting from the inventive metal balloon 14 is that certain metals, such as nitinol, exhibit lubricious surface properties which eliminates the need for surface lubricants found with conventional polymeric balloons. Furthermore, in the embodiment where the inventive metal balloon is made from a superelastic material such as nitinol, the metal balloon may be fabricated such that the low profile configuration is associated with lowest strain state of the balloon such that after inflation the balloon reassumes the low profile configuration under its own superelastic properties. In the embodiment where the inventive metal balloon is made from a shape memory material such as nitinol, the metal balloon may be fabricated such that the low profile configuration is associated with lowest strain high temperature state of the balloon such that after inflation the balloon reassumes the low profile configuration upon the application of heat.

Figure 3:
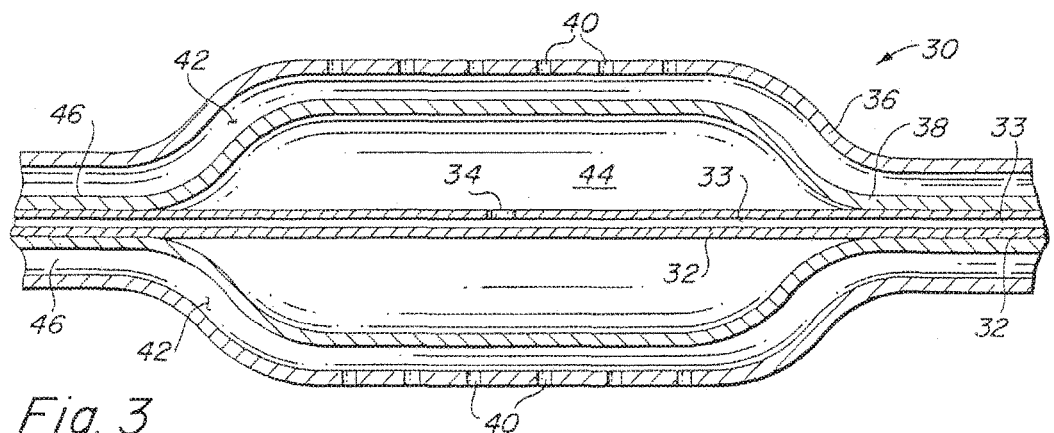
FIG. 3 is a cross-sectional view of a drug delivery metal balloon catheter embodiment.

Turning to FIG. 3 there is illustrated a drug delivery embodiment 30 of the inventive metal balloon catheter. The inventive drug delivery metal balloon catheter 30 consists generally tubular catheter body member 32 defining an inflation lumen 33 and communicating with at least one inflation port 34, a first metal balloon 36 and a second metal balloon 38 in coaxial, spaced-apart concentric relationship with one and other, and an annular lumen 42 intermediate the first metal balloon 36 and the second metal balloon 38, which is in fluid flow communication with an introductory lumen 46. The second metal balloon 38 has a plurality of pores 40 passing therethrough that are in fluid flow communication with the annular lumen 42. The first metal balloon 36 has a solid wall thickness. A bioactive agent, such as a pharmaceutical drug, is introduced into the introductory lumen 46 and passes into the annular lumen 42. The number and size of the plurality of pores 40 are such that the bioactive agent and its carrier will not pass through the pores 40 except under the influence of a positive pressure. A fluid, such as a saline solution, is introduced into inflation lumen 44 through inflation lumen 33, and exerts a positive pressure on second balloon 38 which communicates that positive pressure to any bioactive agent present in annular lumen 42 and first metal balloon 36, and causes dilation of the first metal balloon 36 and the second metal balloon 38 and forces the bioactive agent in annular lumen 42 to pass through the plurality of pores 40 in the first metal balloon 36.

Figure 4:
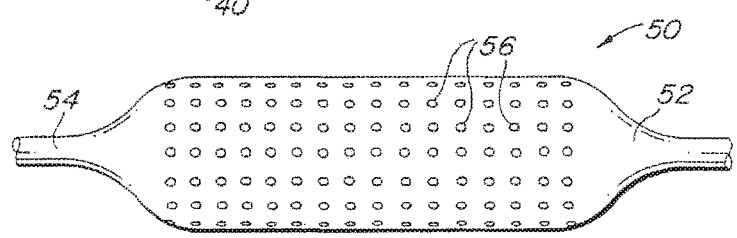
FIG. 4 is a perspective view of a perfusion metal balloon catheter embodiment.

A perfusion metal balloon catheter 50 is illustrated in FIG. 4. The inventive perfusion metal balloon catheter 50 consists generally of a catheter body member 54 and a metal balloon 52 having a plurality of perfusion ports 56 passing through the metal balloon. As with conventional perfusion catheters, body fluids, such as blood, flow into and through the perfusion ports 56 and are perfused with a fluid introduced through the catheter body member 54.

Figure 5:
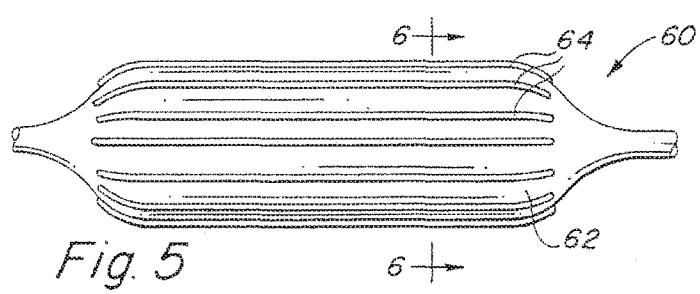
FIG. 5 is an elevational view of an embodiment of a metal balloon surface topography.

Turning to FIGS. 5 and 6 there is illustrated an embodiment of the inventive metal balloon catheter 60 in which the surface topography of the metal balloon 62 is configured to include a plurality of longitudinal beams or projections 64 that project above the surface of the metal balloon 62. By providing the projections 64, the mechanical properties of the metal film comprising the metal balloon 62 are altered to create relatively stronger regions along the longitudinal axis of the projections 64 and relatively weaker regions intermediate adjacent pairs of projections 64. In this configuration, the relatively weaker regions create fold lines for the metal balloon 62 during inflation and deflation of the metal balloon 62. Alternatively, the surface topography of the metal balloon may be configured in such as manner as to provide the projections 64 in a pattern that corresponds to the geometric pattern of an implantable device, such as a stent, such that the implantable device is capable of nesting on the metal balloon 62 between the projections 64 during endoluminal delivery.

Finally, with reference to FIG. 7, there is illustrated an embodiment 70 of the inventive metal balloon catheter in which the metal balloon 72 is coated with an ultra thin coating of a biocompatible elastomer 74. Elastomer 74 adds a compliant component to the metal balloon 72 and serves to encapsulate the metal balloon and protect against fragmenting in the event of metal fatigue and/or cracking of the metal balloon 72.

In accordance with the method of the present invention, vacuum deposition methods as are known in the microelectronics and nano-fabrication arts are preferably employed. It is preferable to employ sputtering or ion beam-assisted evaporative deposition to deposit at least one metal film of a biocompatible metal onto a sacrificial cylindrical substrate. The sacrificial cylindrical substrate has a geometry corresponding to the geometry desired for the inventive metal balloon, and at least one of a plurality of metal film layers are deposited onto the sacrificial cylindrical substrate. After depositing a film having a desired thickness between 0.1 µm and 25 µm, the substrate and the deposited film are removed from the deposition chamber and the sacrificial substrate is removed by means suitable for the selected substrate. For example, a copper substrate may be employed, then sacrificially removed by chemical etching. Any patterning of nesting regions for a stent and/or projections for creating fold lines for the balloon may be imparted either by depositing metal species through a mask or by etching regions of a deposited film. The entire metal balloon or selected regions of the metal balloon may be subject to post-deposition annealing to alter the crystalline structure of the metal film and effect changes in the material properties of the metal film, such as altering the transition temperature of the annealed regions as well as to create advantageous zero stress-strain configurations such as low profile folds.

Figure 8:
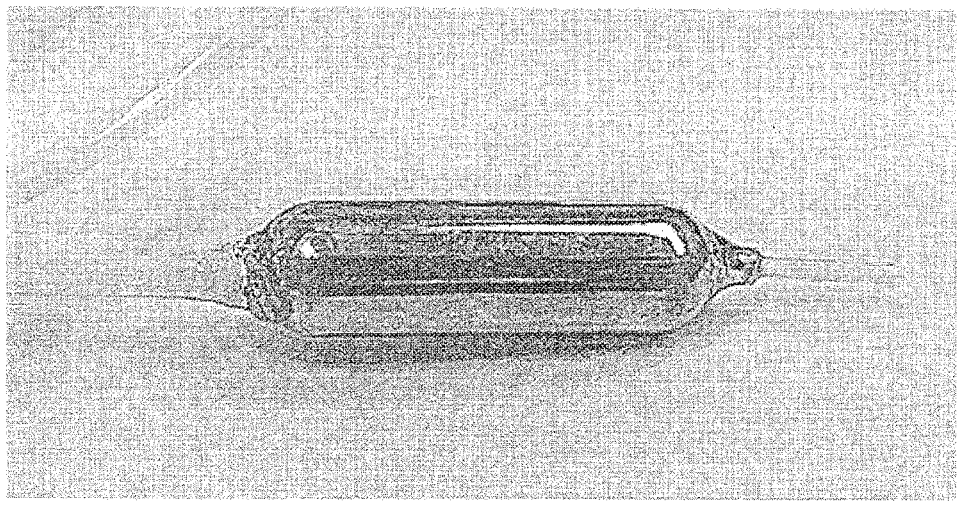
FIG. 8 is a photograph of the inventive metal balloon catheter.
Figure 9:
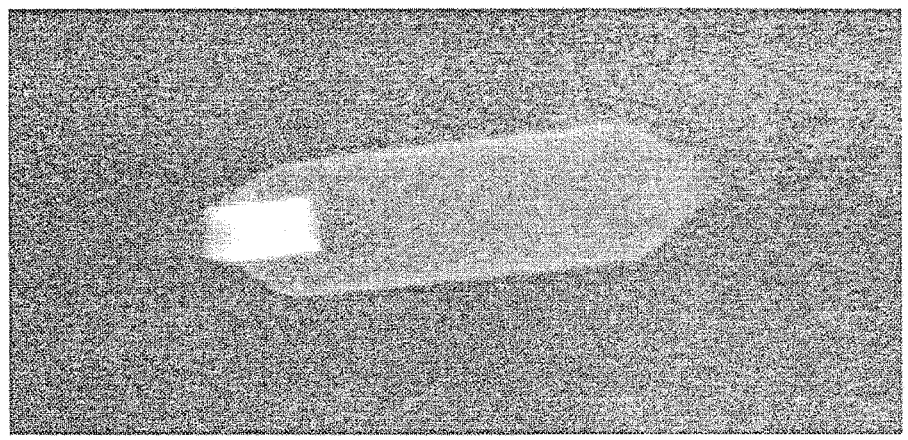
FIG. 9 is a photograph of the inventive metal balloon catheter under x-ray imaging.

FIGS. 8 and 9 illustrate the inventive metal balloon catheter fabricated by sputter depositing nickel-titanium alloy onto a copper mandrel, etching the copper mandrel to release the deposited metal balloon, and adhering the metal balloon onto a polymeric catheter body using a cyanoacrylate biocompatible adhesive to attach proximal and distal portions of the metal balloon.

FIGS. 10A-10D depict the inventive metal balloon 110 in its inflated state (FIG. 10A) having proximal 112 and distal 114 taper sections and an intermediate enlarged tubular section 118. In accordance with one embodiment of the invention, the metal balloon 110 may be imparted with an deflated geometry as depicted in FIG. 10B in which the intermediate section 118 and the proximal 112 and distal 114 taper sections deflate to form a configuration with a plurality of leaflets 120 that project radially outwardly from the longitudinal axis of the metal balloon 110. FIG. 10C is an end view of FIG. 10B. FIG. 10D depicts folding of the leaflets 120 in order to accommodate endoluminal delivery or removal of the metal balloon 110.

The deflated geometry depicted in FIG. 10B may be imparted by a wide variety of means, including, without limitation, shape memory or superelastic properties of the metal material, fold or score lines along the metal balloon 110 defining fold regions for the leaflets 120, or thickened regions of the metal balloon 110 intermediate the leaflets 120 that offer greater resistance to folding upon deflation of the metal balloon 110.

In accordance with the preferred embodiment of fabricating the inventive microporous metallic implantable device in which the device is fabricated from vacuum deposited nitinol tube, a cylindrical deoxygenated copper substrate is shaped into a geometrical configuration corresponding to an inflated angioplasty balloon having proximal and distal tapers. The substrate is mechanically and/or electropolished to provide a substantially uniform surface topography for accommodating metal deposition thereupon. A cylindrical hollow cathode magnetron sputtering deposition device was employed, in which the cathode was on the outside and the substrate was positioned along the longitudinal axis of the cathode. A cylindrical target consisting either of a nickel-titanium alloy having an atomic ratio of nickel to titanium of about 50-50% and which can be adjusted by spot welding nickel or titanium wires to the target, or a nickel cylinder having a plurality of titanium strips spot welded to the inner surface of the nickel cylinder, or a titanium cylinder having a plurality of nickel strips spot welded to the inner surface of the titanium cylinder is provided. It is known in the sputter deposition arts to cool a target within the deposition chamber by maintaining a thermal contact between the target and a cooling jacket within the cathode. In accordance with the present invention, it has been found useful to reduce the thermal cooling by thermally insulating the target from the cooling jacket within the cathode while still providing electrical contact to it. By insulating the target from the cooling jacket, the target is allowed to become hot within the reaction chamber. Two methods of thermally isolating the cylindrical target from the cooling jacket of the cathode were employed. First, a plurality of wires having a diameter of 0.0381 mm were spot welded around the outer circumference of the target to provide an equivalent spacing between the target and the cathode cooling jacket. Second, a tubular ceramic insulating sleeve was interposed between the outer circumference of the target and the cathode cooling jacket. Further, because the Ni—Ti sputtering yields can be dependant on target temperature, methods which allow the target to become uniformly hot are preferred.

The deposition chamber was evacuated to a pressure less than or about $2\text{-}5\times10^{-7}$ Torr and pre-cleaning of the substrate is conducted under vacuum. During the deposition, substrate temperature is preferably maintained within the range of 300 and 700 degrees Centigrade. It is preferable to apply a negative bias voltage between 0 and −1000 volts to the substrate, and preferably between −50 and −150 volts, which is sufficient to cause energetic species arriving at the surface of the substrate. During deposition, the gas pressure is maintained between 0.1 and 40 mTorr but preferably between 1 and 20 mTorr. Sputtering preferably occurs in the presence of an Argon atmosphere. The argon gas must be of high purity and special pumps may be employed to reduce oxygen partial pressure. Deposition times will vary depending upon the desired thickness of the deposited tubular film. After deposition, the plurality of microperforations are formed in the tube by removing regions of the deposited film by etching, such as chemical etching, ablation, such as by excimer laser or by electric discharge machining (EDM), or the like. After the plurality of microperforations are formed, the formed microporous film is removed from the copper substrate by exposing the substrate and film to a nitric acid bath for a period of time sufficient to remove dissolve the copper substrate.

While the present invention has been described with reference to its preferred embodiments, those of ordinary skill in the art will understand and appreciate that variations in materials, dimensions, geometries, and fabrication methods may be or become known in the art, yet still remain within the scope of the present invention which is limited only by the claims appended hereto.

What is claimed is:

1. A catheter comprising: at least two balloons, the at least two balloons comprising a first metallic balloon, the first metallic balloon having a solid balloon thickness, the balloon thickness consisting of metal, and a second polymer balloon, the at least two balloons positioned concentrically relative to each other and at least one annular lumen defined there between.

2. The catheter of claim 1, wherein the first metallic balloon further comprises a polymer outer coating.

3. The catheter of claim 2, wherein the polymer outer coating is an elastomer coating disposed onto an outer surface of the first metallic balloon and is adapted to contain the first metallic balloon upon fragmenting or cracking of the first metallic balloon.

4. The catheter of claim 1, wherein the second polymer balloon further comprises an elastomer.

5. The catheter of claim 1, wherein at least one of the at least two balloons further comprises a plurality of perfusion ports passing through the at least one of the at least two balloons and facilitating fluid flow communication between outside and inside of the at least one of the at least two balloons.

6. The catheter of claim 1, wherein at least one of the at least two balloons further comprises a plurality of generally longitudinal projections emanating from an exterior surface of the at least one of the at least two balloons and extending along a longitudinal axis thereof.

7. The catheter of claim 6, wherein adjacent pairs of generally longitudinal projections define fold lines for the at least one of the at least two balloons.

8. The catheter of claim 6, wherein the generally longitudinal projections form a geometric pattern that is physically complementary to an implantable device that rests on the at least one of the at least two balloons and is delivered by the catheter.

* * * * *